US011143645B2

(12) United States Patent
Hughes et al.

(10) Patent No.: US 11,143,645 B2
(45) Date of Patent: Oct. 12, 2021

(54) SYSTEMS AND METHODS FOR A VERSATILE ELECTROCHEMICAL TEST STRIP THAT MAY INCLUDE ONE OR MORE ASSAYS FOR DIFFERENT ANALYTES IN THE SAME TEST STRIP

(71) Applicant: Polymer Technology Systems, Inc., Indianapolis, IN (US)

(72) Inventors: Gary L. Hughes, Camby, IN (US); Aniruddha Patwardhan, Fishers, IN (US)

(73) Assignee: POLYMER TECHNOLOGY SYSTEMS, INC., Whitestown, IN (US)

( * ) Notice: Subject to any disclaimer, the term of this patent is extended or adjusted under 35 U.S.C. 154(b) by 3 days.

(21) Appl. No.: 15/382,389

(22) Filed: Dec. 16, 2016

(65) Prior Publication Data

US 2017/0176410 A1    Jun. 22, 2017

Related U.S. Application Data

(60) Provisional application No. 62/268,962, filed on Dec. 17, 2015.

(51) Int. Cl.
  *G01N 27/327*  (2006.01)
  *G01N 33/49*  (2006.01)
  *G01N 33/487*  (2006.01)

(52) U.S. Cl.
  CPC ....... *G01N 33/492* (2013.01); *G01N 27/3273* (2013.01); *G01N 33/48707* (2013.01); *G01N 27/3272* (2013.01)

(58) Field of Classification Search
  CPC .................. G01N 27/3272; G01N 27/3273
  See application file for complete search history.

(56) References Cited

U.S. PATENT DOCUMENTS 5,264,103 A * 11/1993 Yoshioka ............... C12Q 1/004
                                                                204/403.1
5,266,179 A * 11/1993 Nankai ............. G01N 33/48771
                                                                204/401

(Continued)

FOREIGN PATENT DOCUMENTS

EP      0537761 A2    4/1993
EP      1396717 A1    3/2004

(Continued)

OTHER PUBLICATIONS

International Search Report and Written Opinion dated Feb. 23, 2017 issued in related PCT App. No. PCT/US2016/067361 (13 pages).

(Continued)

*Primary Examiner* — Alexander S Noguerola
(74) *Attorney, Agent, or Firm* — Haynes and Boone, LLP

(57) ABSTRACT

A test strip for electrochemical testing of a blood analyte includes a plurality of test sites for the electrochemical testing of analytes on a single test strip. Each test site includes a first receiving port, the first receiving port for receiving a blood sample, the first receiving port at a first end of the test strip. The test site further includes a first electrode and a second electrode, the first and second electrodes proximate to the first receiving port. Each test site further includes a first contact and a second contact, the first and second contacts at a second end of the test strip, the first and second contacts interconnected with the first and second electrodes, respectively.

5 Claims, 5 Drawing Sheets

(56) References Cited

U.S. PATENT DOCUMENTS

| | | | | |
|---|---|---|---|---|
| 5,282,950 | A * | 2/1994 | Dietze | G01N 27/3273 |
| | | | | 204/406 |
| 5,582,697 | A * | 12/1996 | Ikeda | C12Q 1/001 |
| | | | | 204/403.11 |
| 5,589,045 | A * | 12/1996 | Hyodo | G01N 33/48792 |
| | | | | 204/403.11 |
| 6,849,237 | B2 * | 2/2005 | Housefield | A61B 5/0002 |
| | | | | 204/403.03 |
| 6,893,545 | B2 * | 5/2005 | Gotoh | C12Q 1/005 |
| | | | | 204/401 |
| 7,323,098 | B2 * | 1/2008 | Miyashita | C12Q 1/004 |
| | | | | 204/403.14 |
| 7,625,473 | B2 * | 12/2009 | Hsu | G01N 33/48771 |
| | | | | 204/400 |
| 9,354,194 | B2 * | 5/2016 | Rodgers | G01N 27/3272 |
| 2003/0203498 | A1 | 10/2003 | Neel et al. | |
| 2011/0094896 | A1 | 4/2011 | Macfie et al. | |
| 2011/0184264 | A1 | 7/2011 | Galasso et al. | |
| 2013/0277232 | A1 | 10/2013 | Bar-Or et al. | |

FOREIGN PATENT DOCUMENTS

| | | |
|---|---|---|
| EP | 2672261 A1 | 12/2013 |
| WO | WO 2004/113910 A1 | 12/2004 |
| WO | WO 2008/130920 A1 | 10/2008 |
| WO | WO 2015/075170 A1 | 5/2015 |

OTHER PUBLICATIONS

European Search Report dated Jun. 25, 2019 issued in co-pending European patent application No. 16876858.8 (9 pages).

* cited by examiner

SYSTEMS AND METHODS FOR A VERSATILE ELECTROCHEMICAL TEST STRIP THAT MAY INCLUDE ONE OR MORE ASSAYS FOR DIFFERENT ANALYTES IN THE SAME TEST STRIP

CROSS REFERENCE TO RELATED APPLICATION

This application claims the benefit of U.S. Provisional Patent Application 62/268,962 filed Dec. 17, 2015, and hereby incorporated by reference to the same extent as though fully disclosed herein.

BACKGROUND

Point of Care ("POC") and home testing for various blood analytes and other detectable metrics in bodily fluids is desirable for patient and doctor. Two primary types of test strips are available for testing for blood analytes. These test strips include electrochemical and optical test strips. Optical test strips rely on a color change reaction resulting from the presence of an analyte. A light then is shone on the test strip and an optical feature of the test strip then is measured. Optical features include, but are not limited to, reflectance, absorption, and color. In an electrochemical test strip, a voltage, amperage, capacitance, or other electric feature is measured by two or more electrodes that contact the sample. In many scenarios, the test strips may include printed circuit pathways and reagent coatings on the two or more electrodes. Generally, it is thought that electrochemical strips are less expensive to manufacture and are generally thought to be more reliable. However, electrochemical strips have not generally been adapted to include multiple tests.

BRIEF SUMMARY

In one embodiment, a test strip for electrochemical testing of a blood analyte includes a first receiving port, the first receiving port for receiving a blood sample, and the first receiving port at a first end of the test strip. The test strip further includes a first electrode and a second electrode, the first and second electrodes proximate to the first receiving port. The test strip further includes a first contact and a second contact, the first and second contacts at a second end of the test strip, the first and second contacts interconnected with the first and second electrodes, respectively. Optionally, one of the first and second electrodes includes a reagent on a surface of one of the first and second electrodes. In one alternative, the reagent is painted on to the one of the first and second electrodes. In another alternative, the test strip further includes a second receiving port, the second receiving port proximate to the first receiving port of the first end of the test strip; a third electrode and a fourth electrode, the third and fourth electrodes proximate to the second receiving port; and a third contact and a fourth contact, the third and fourth contacts at the second end of the test strip and interconnected with the third and fourth electrodes, respectively. Optionally, the test strip further includes a fifth contact and a sixth contact, the fifth and sixth contacts interconnected to provide for an insertion indication when the test strip is inserted into a meter. Alternatively, the first receiving port and the second receiving port are on opposite sides of the test strip, such that one is underneath the other. Optionally, the test strip has between zero to three additional sample receiving ports; and the test strip has dimensions, wherein the dimensions are the same regardless of the number of additional sample receiving ports. In one configuration, the test strip further includes a reference electrode, the reference electrode proximate to the first and second electrodes. In another configuration, the test strip further includes a third electrode and a fourth electrode, the third and fourth electrodes proximate to the first receiving port; and a third contact and a fourth contact, the third and fourth contacts at a second end of the test strip, the third and fourth contacts interconnected with the third and fourth electrodes, respectively. In another configuration, the test strip further includes a fifth electrode and a sixth electrode, the fifth and sixth electrodes proximate to the first receiving port; and a fifth contact and a sixth contact, the fifth and sixth contacts at a second end of the test strip, the fifth and sixth contacts interconnected with the fifth and sixth electrodes, respectively.

In one embodiment, a test strip and meter combination system for electrochemical testing of a blood analyte includes a test strip and a meter. The test strip includes a first receiving port, the first receiving port for receiving a blood sample, and the first receiving port at a first end of the test strip. The test strip further includes a first electrode and a second electrode, the first and second electrodes proximate to the first receiving port. The test strip further includes a first contact and a second contact, the first and second contacts at a second end of the test strip, the first and second contacts interconnected with the first and second electrodes, respectively. The meter has a test strip receiving port shaped to receive the test strip, the meter including a plurality of contacts, a first portion of the plurality of contacts positioned to interface with the first and second contacts. Optionally, one of the first and second electrodes includes a reagent on a surface of one of the first and second electrodes. In one configuration, the reagent is painted on to the one of the first and second electrodes. In one alternative, the system further includes a second receiving port, the second receiving port proximate to the first receiving port of the first end of the test strip; a third electrode and a fourth electrode, the third and fourth electrodes proximate to the second receiving port; and a third contact and a fourth contact, the third and fourth contacts at the second end of the test strip and interconnected with the third and fourth electrodes, respectively, wherein a second first portion of the plurality of contacts is positioned to interface with the third and fourth contacts. Optionally, the system further includes a fifth contact and a sixth contact on the test strip, the fifth and sixth contacts interconnected to provide for an insertion indication when the test strip is inserted into the meter, and a third portion of the plurality of contacts positioned to interface with the fifth and sixth contacts. Alternatively, the system further includes the first receiving port and the second receiving port wherein the ports are on opposite sides of the test strip, such that one is underneath the other. Optionally, the test strip has between zero to three additional sample receiving ports; and the test strip has dimensions, wherein the dimensions are the sample regardless of the number of additional sample receiving ports. Optionally, the meter includes a plurality of interfacing portions of the plurality of contacts which are each positioned to interface with each set of contacts corresponding to a receiving port. Alternatively, the system further includes a reference electrode in the test strip, the reference electrode proximate to the first and second electrodes. Optionally, the test strip of the system further includes a third electrode and a fourth electrode, the third and fourth electrodes proximate to the first receiving port; and a third contact and a fourth contact, the third and fourth contacts at a second end of the test strip, the third and fourth contacts interconnected with the third and fourth electrodes, respectively. Optionally, the test strip of the system further includes a fifth electrode and a sixth electrode, the fifth and sixth electrodes proximate to the first receiving port; and a fifth contact and a sixth contact, the fifth and sixth contacts at a second end of the test strip, the fifth and sixth contacts interconnected with the fifth and sixth electrodes, respectively.

DETAILED DESCRIPTION

Figure 1:
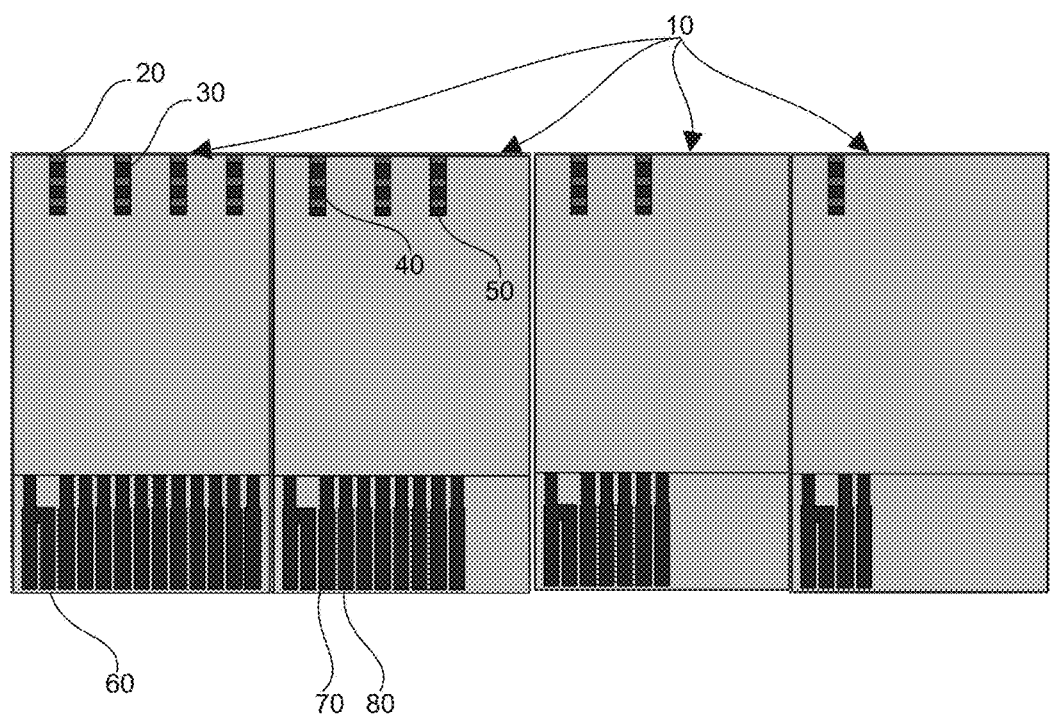
FIG. 1 shows one embodiment of a flexible electrochemical test strip having multiple single analyte tests.

Certain terminology is used herein for convenience only and is not to be taken as a limitation on the embodiments of the systems and methods for a versatile electrochemical test strip that may include one or more assays for different analytes in the same test strip. In the drawings, the same reference letters are employed for designating the same elements throughout the several figures. In many embodiments, a versatile electrochemical test strip is provided that may include one or more assays for different analytes in the same test strip. Embodiments of the electrochemical test strips may fit with a standardized meter that may equally receive strips that have a single sample and set of electrodes and strips that have multiple analytes.

Having a single electrochemical test strip is not as advantageous as having a panel of electrochemical tests. Due to the large effort in developing meters, it is not desirable to engineer an analyzer for two analyte electrochemical strips, another meter for three analyte tests, and yet another meter for four analyte tests. Instead, it is desirable to have a single meter that receives a variety of test strips. In order to accomplish this, in some embodiments, a standardized test strip is provided that may provide for between one to eight or more different tests for different analytes. In many embodiments, any number of tests may be included in a single test strip. As more and more electrochemical assays are developed, there is a need for an electrochemical analyzer that will allow for one to four (or possibly more) combinations. By providing a meter that may receive a variety of test strips, the meter may support an evolving offering of electrochemical test strips.

Embodiments of the system including configurable test strips and a flexible meter to receive them provides for a next generation electrochemical meter that will handle test panels and a strip design that will allow for single or multiple assay formats. Specifically, the design:

1. Allows the manufacturer to build a meter and allow assay development to catch up instead of having several meter versions evolving throughout the product development life cycle;
2. Provides one electrochemical port designed to fit one strip. There will not be a port for single electrochemical tests, another port for dual electrochemical tests, etc.;
3. Affords the manufacturer the ability to have multi-analyte electrochemical panels. The strip is versatile enough to have one or multiple tests depending on the customer's desires; and
4. This versatile strip solution would allow for the manufacturing of any combination of electrochemical assays that were developed. The following are just a few combinations possible:
   Lipid Panel+Glucose–Cholesterol, HDL, Triglycerides, Glucose
   Lipid Panel–Cholesterol, HDL, Triglycerides
   Diabetic Panel–Glucose, Ketones, Triglycerides
   Chol+Glu–Cholesterol, Glucose
   Glucose.

Devices exist that provide for a single electrochemical analyte, such as POCket Lipid® that sells an electrochemical lipid panel. However, such systems do not have the flexibility to test a single electrochemical test like glucose. Nor do the systems provide for a strip that may be modified to handle a wide variety of analyte strips and multi-analyte combinations.

In embodiments of the strip disclosed, the strip size does not change based on the number of assays that are loaded onto it. There is one connection port whether the test is a single test or a multi-analyte panel test.

With the advent of the amperometric glucose test strip, many diagnostic companies have looked for other novel ways to use this technology. Electrochemical assays hold certain advantages such as speed of testing, a minimal volume of blood, excellent precision, easily manufactured and calibrated meters, minimal reagent, etc. It appears that Acon, i-Sens, Infopia, Roche, Ambisea, ApexBio, Bioptik, General Life, SD Biosensors, and Techno Medica are all in some stage of developing electrochemical lipid test strips according to their own admission. However, having an assay is not nearly as advantageous as having multiple assays in a panel format. Embodiments of the test strip disclosed herein, as designed, will allow for one electrochemical port that will receive a versatile strip. This strip is designed to be manufactured to have one or many assays positioned on it. By using this strip design, a meter may be built and sold allowing the future assay development to follow later.

FIG. 1 shows one embodiment of the strip design. Shown are four strips 10. From left to right, the strips 10 have 4, 3, 2, and 1 sample receiving ports 20. Each sample receiving port may have an electrode 30, a counter electrode 40, and a reference electrode 50. The reference electrode 50 may provide for a fill indication, as it will only pass a voltage when the sample reaches the electrode 50. The contacts 70, 80 are also visible, which interconnect with the electrodes and connect to contacts in the meter when inserted. The strip size does not change depending on the number of assays. In addition, the electrode placement does not change depending on the type of assays. Depending on what is desired for the testing scheme, sheets are printed for one, two, three, or four analytes. The spirit behind this invention disclosure is not to limit the size of the panel to only four analytes, but to provide a concept that is protected whether one or ten analytes are tested. Also, the electrodes do not all need to be on one side of the strip. Superior technology may be able to place electrodes on both sides of the strip, thus allowing for miniaturization.

Whatever the arrangement of electrodes is, the meter will have corresponding contacts to interface with the contacts of the electrodes. Therefore, a flexible system can be created, whereby the meter includes contacts for the maximum number of expected electrodes. The maximum number of expected electrodes will be 4 or more in most scenarios. Typically, each tests area shall include two electrodes or more for testing for the analyte of interest. When the strip is inserted into the device, the meter may be automatically configured for the actual number of electrodes on the strip and the particular analytes it is measuring. This configuration is based on the meter identifying the type of test strip and executing code accordingly.

Flexibility in the system results from providing a standard size cassette with the option for multiple assays in the single cassette. In various embodiments, the meter associated with the test strip is configured only measures and activates certain contacts that are aligned for engaging the electrodes of the test strip. In some embodiments, a single capillary tube in the test strip may receive a sample (blood typically). The capillary tube may include numerous electrodes, all of which test for a different analyte. In such embodiments a variety of measurements may need to be taken between each positive electrode and every negative electrode, such that cross talk interference can be calculated and eliminated.

Figure 4:
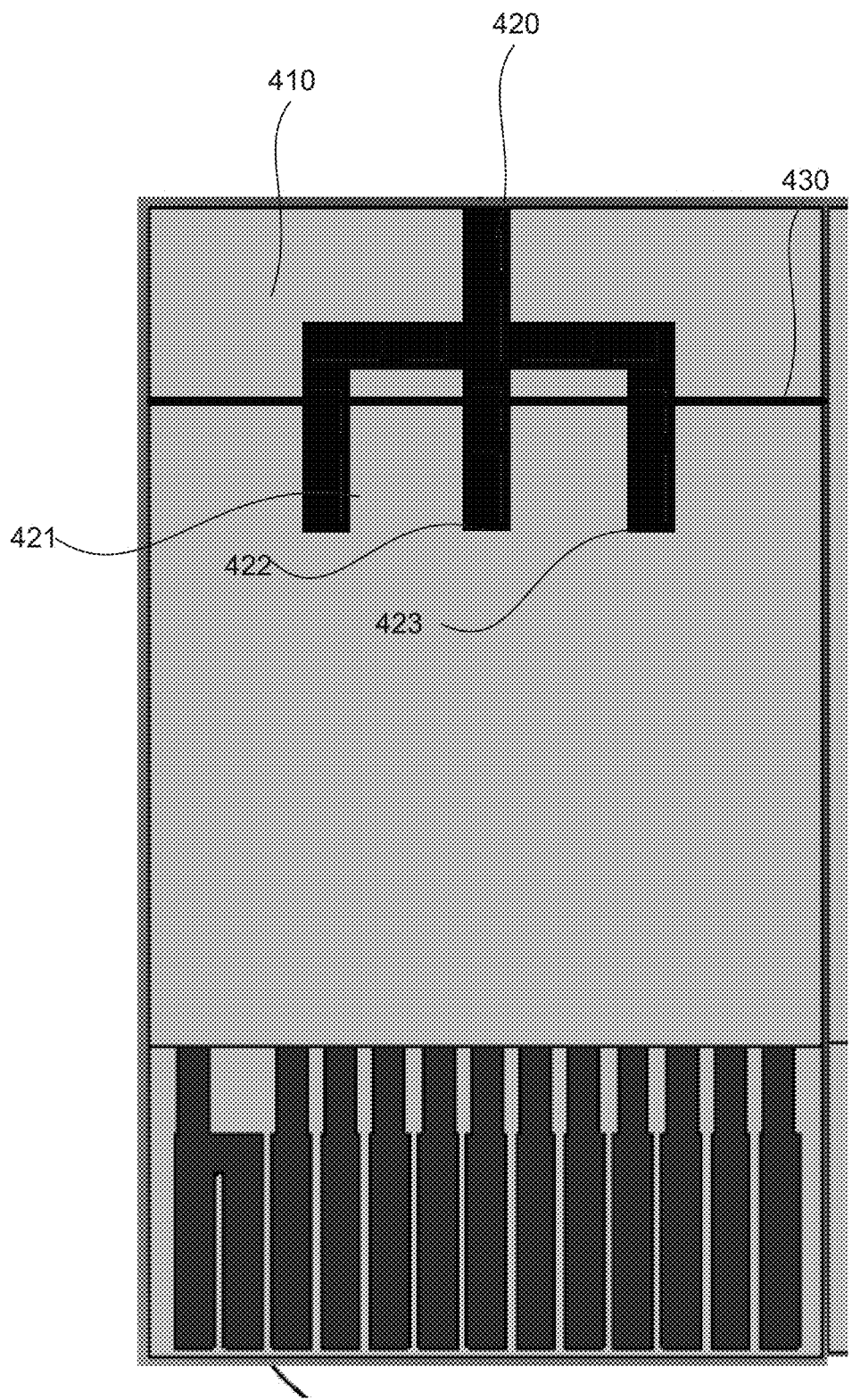
FIG. 4 shows one embodiment of a test strip with multiple branch capillary channels.
Figure 5:
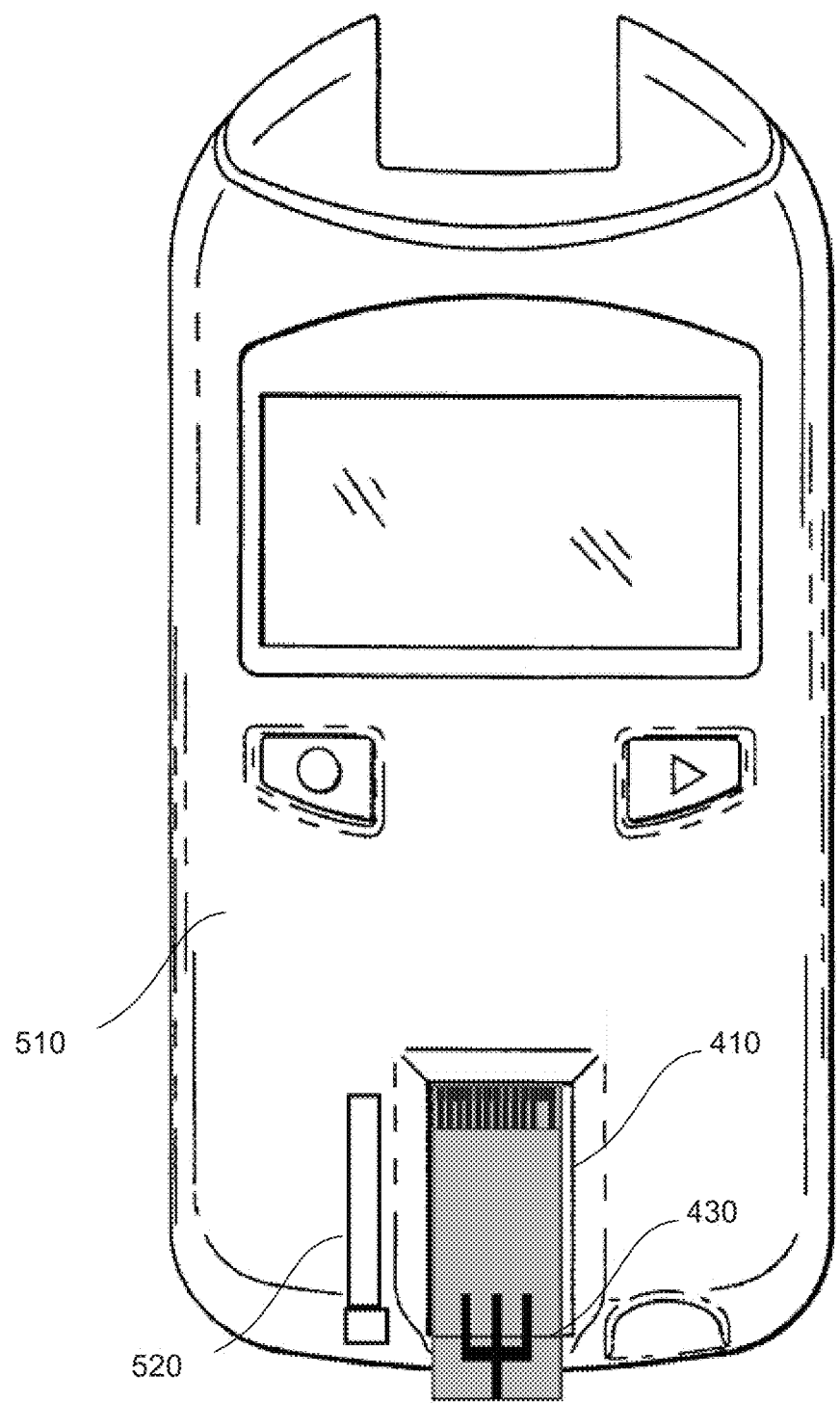
FIG. 5 shows one embodiment of a meter interfaced with the test strip of FIG. 4.

In some embodiments a single capillary channel breaks into multiple capillary channels. Such an embodiment of a test strip 410 is shown in FIG. 4. The electrodes that extend into the tubes are not shown, but each branch 421, 422, 423 of capillary tube 420 has associated electrodes. Since blood flows between the branches 421, 422, 423, cross talk must be calculated for. The view as shown is a cut away view and in an actual product the channels would not be visible. In some alternatives, the channels are visible, via a clear plastic top of the test strip 410. Additionally, in some embodiments, the test strip 410 includes separator 430. Such a separator 430 may take many embodiments. In some embodiments, the separator 430 is a fold line, whereby the test strip may be folded, effectively separating the branches. Alternatively, it may be a clamp or pinching apparatus. Alternatively, it may be a slide in the test strip that slides across a channel, thereby cutting off the capillary tubes. It is thought that the folding methodology across separator 430 will yield simply and efficient results. In some embodiments, the meter will include an arm that provides a pressure force or folds down to hold the fold of the test strip in place such that the branches are separated. Such an embodiment is shown in FIG. 5. In FIG. 5, strip 410 has been inserted into meter 510. As shown, the strip may be folded at separator 430 and then arm 520 may be folded down across the strip insertion area in order to hold the fold in place. Alternatively, the arm 520 may provide pressure force to the strip 410, also resulting in the branches of the strip being separated.

In some embodiments, single analyte test strips are designed to have the same location with at least four associated electrodes. The electrode 60 that appears as an "h" is used for strip detection by the meter. The remaining assays will have at least three electrodes—one for sample fill detection and the other two as a counter electrode and a working electrode. These assays are not limited to a set number of electrodes, for it is foreseen in some embodiments that more electrodes may be added for purposes of determining and correcting for hematocrit or other interfering substances. In addition to electrode 60 providing for detection of the insertion of the strip into the meter, in alternative configurations, electrode 60 may provide for an indication of the type of strip inserted. This may be configured by replacing electrode 60 with a micro memory, that not only provides for recognition of insertion, but additionally provides for a code or other information that identifies the strip inserted. Additionally, in some scenarios, the calibration curve(s) for the strip, or other information may be stored and accessed accordingly.

In multiple configurations, reagents may be painted on the electrodes. Alternatively, reagents may be printed, coated, dip coated, or otherwise applied, as will be apparent in the field. Various types of electrodes may be used as well, including those made of carbon, gold, platinum, copper, or other conductive materials, as will be apparent to those in the field.

Figure 2:
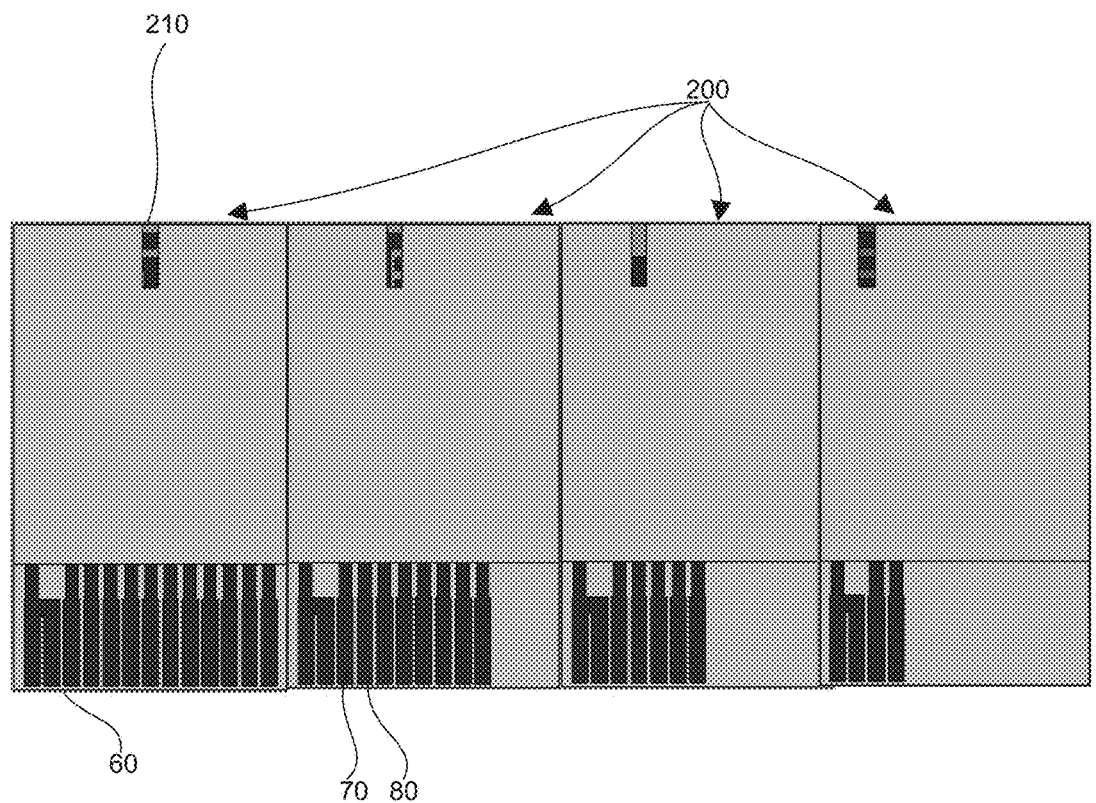
FIG. 2 shows another embodiment of a flexible electrochemical test strip having multiple analyte tests.
Figure 3:
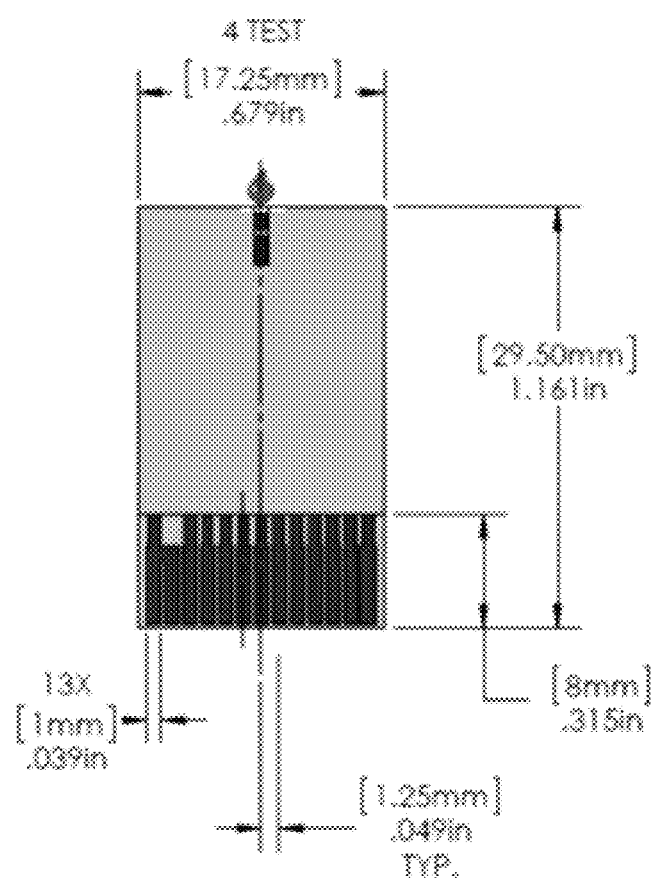
FIG. 3 shows one embodiment of a flexible electrochemical test strip showing possible dimensions.

FIG. 1 displays separate blood sampling port for each assay. Some embodiments may include separate sampling ports, particularly if there could be "cross talk" between reagents. FIG. 2 shows such an embodiment. In many embodiments, there will be a singular sampling port 210 for the multi-analyte panels. Again, this strip allows for adaptability of design to meet the needs of particular assays. As shown in the left-most strip, a single sample port 210 may provide for five different sets of contacts, providing for the testing of five different analyte tests. FIG. 3 shows exemplary dimensions for the test strip.

It is important to note that the design of this strip allows for each assay to be completely independent from the other tests. Each assay will have its own sample well with a fill detection system. For example, for the embodiment of having one sampling port, if the blood reaches assay #4 last, the test will not start until the fluid has been detected. The tests will be completely independent in timing, voltage applied, and even electrodes. It is possible to envision strips where some assays use carbon electrodes, and others may employ another conductive material on the same strip.

Another advantage to this versatile strip design is that is not limited to the type of electrochemical testing. It is envisioned that the connecting port will be connected to a meter on a chip such as Analog Devices' ADuCM350®. This chip allows for a self-calibrating meter and is capable of supplying the different test conditions with the precise voltage for the designated time. The chip provides the ability of each assay to be independent from the other. Furthermore, the ADuCM350® can supply both positive and negative voltage to an assay, depending on the requirements of the test.

By placing a MEMo chip or lot code chip into the meter, the meter is prompted for the panel that will be tested. The meter may be programmed so that if a four-analyte electrochemical MEMo chip is in the meter, but a two-analyte strip (or any strip that does not have four assays) is tested, it will give the user an error code. To allow for easy recognition and to avoid error, the electrochemical test strips may be color coded to match the proper MEMo chip.

In conclusion, embodiments of an electrochemical test strip are provided that will allow for one assay or multiple assays to be situated on it. The strip will use a singular connecting port on the meter allowing for independent multi-analyte tests. This will provide an electrochemical panel platform from which to launch currently developed assays and allow others to follow.

In many embodiments, parts of the system, especially the meter, are provided in devices including microprocessors. Various embodiments of the systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of the systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A test strip and meter combination system for electrochemical testing of a blood analyte, the system comprising:
    a first test strip including:
        a first receiving port, the first receiving port for receiving a blood sample, the first receiving port at a first end of the first test strip;
        a first electrode and a second electrode, the first and second electrodes proximate to the first receiving port;
        a first contact and a second contact, the first and second contacts at a second end of the first test strip, the first and second contacts interconnected with the first and second electrodes, respectively; and
        a second receiving port, the second receiving port proximate to the first receiving port of the first end of the first test strip;
        a third electrode and a fourth electrode, the third and fourth electrodes proximate to the second receiving port; and
        a third contact and a fourth contact, the third and fourth contacts at the second end of the first test strip and interconnected with the third and fourth electrodes, respectively;
        a reference electrode;
    a second test strip including:
        a third receiving port, the third receiving port for receiving a blood sample, the third receiving port at a first end of the second test strip;
        a fifth electrode and a sixth electrode, the fifth and sixth electrodes proximate to the third receiving port;
        a fifth contact and a sixth contact, the fifth and sixth contacts at a second end of the second test strip, the fifth and sixth contacts interconnected with the fifth and sixth electrodes, respectively; and
    a meter, the meter having a test strip receiving port shaped to receive one of the first test strip and the second test strip, the meter including a plurality of contacts, when the first test strip is inserted a first portion of the plurality of contacts positioned to interface with the first and second contacts; the reference electrode and meter are configured to provide a fill indication when reached by a sample, wherein a second portion of the plurality of contacts are further positioned to interface with a fifth and sixth contact, and when the second test strip is inserted the first portion of the plurality of contacts interfacing with the fifth and sixth contact and the second portion of the plurality of contacts are unused when interfacing with the first test strip, wherein the meter is configured to receive a first chip associated with the first test strip, the first chip containing instructions executable by the meter and configuring the meter to give an error code when the first chip is inserted into the meter and the second test strip is inserted into the meter, based on the first and second test strip include a different number of contacts.

2. The system of claim 1, wherein one of the first and second electrodes includes a reagent on a surface of one of the first and second electrodes.

3. The system of claim 2, wherein the reagent is painted on to the one of the first and second electrodes.

4. The system of claim 1, wherein the first receiving port and the second receiving port are on opposite sides of the first test strip, such that one is underneath the other.

5. A test strip and meter combination system for electrochemical testing of a blood analyte, the system comprising:
    a first test strip including, a first testing site and a first set of contacts;
    a second test strip including, a second testing site and a second set of contacts and a third testing site and a third set of contacts;
    a meter, the meter having a test strip receiving port shaped to receive one of the first test strip and the second test strip, the meter including a plurality of contacts such that when the first test strip is inserted a first portion of the plurality of contacts interface with the first set of contacts and a second portion of the plurality of contacts are unused when interfacing with the first test strip and when the second test strip is inserted the first portion of the plurality of contacts interface with the second set of contacts and the second portion of the plurality of contacts interface with the second set of contacts, wherein the meter is configured to receive a first chip associated with the first test strip, the first chip containing instructions executable by the meter and configuring the meter to give an error code when the first chip is inserted into the meter and the second test strip is inserted into the meter, based on the first and second test strip include a different number of contacts.

* * * * *